(12) United States Patent
Brin et al.

(10) Patent No.: US 7,846,456 B2
(45) Date of Patent: *Dec. 7, 2010

(54) METHODS FOR BREAST TREATMENT

(75) Inventors: Mitchell F. Brin, Newport Beach, CA (US); Stephen Donovan, Capistrano Beach, CA (US)

(73) Assignee: Allergan, Inc., Irvine, CA (US)

( * ) Notice: Subject to any disclaimer, the term of this patent is extended or adjusted under 35 U.S.C. 154(b) by 987 days.

This patent is subject to a terminal disclaimer.

(21) Appl. No.: 11/192,777

(22) Filed: Jul. 29, 2005

(65) Prior Publication Data

US 2005/0260231 A1    Nov. 24, 2005

Related U.S. Application Data

(60) Division of application No. 10/071,826, filed on Feb. 8, 2002, which is a continuation-in-part of application No. 09/631,221, filed on Aug. 2, 2000, now abandoned, which is a continuation-in-part of application No. 09/454,842, filed on Dec. 7, 1999, now Pat. No. 6,139,845.

(51) Int. Cl.
*A61K 39/02* (2006.01)
*A61K 39/00* (2006.01)
*A61K 39/38* (2006.01)
*A61K 39/08* (2006.01)
*A61K 38/00* (2006.01)
*A01K 37/18* (2006.01)

(52) U.S. Cl. ............... 424/236.1; 424/184.1; 424/234.1; 424/239.1; 424/247.1; 514/2

(58) Field of Classification Search .................. None
See application file for complete search history.

(56) References Cited

U.S. PATENT DOCUMENTS

| | | |
|---|---|---|
| 5,183,462 A | 2/1993 | Borodic |
| 5,437,291 A | 8/1995 | Pasricha et al. |
| 5,670,484 A | 9/1997 | Binder |
| 5,766,605 A | 6/1998 | Sanders et al. |
| 6,063,768 A | 5/2000 | First |
| 6,139,845 A | 10/2000 | Donovan |
| 6,312,708 B1 * | 11/2001 | Donovan ............. 424/423 |
| 2001/0043930 A1 * | 11/2001 | Aoki et al. ........... 424/184.1 |

FOREIGN PATENT DOCUMENTS

| | | |
|---|---|---|
| DE | 19802569 A1 | 1/1998 |
| GB | 2142032 | 1/1985 |
| GB | 2142032 A | 1/1985 |
| WO | WO 94/24155 | 10/1994 |
| WO | WO 00/33880 | 6/2000 |
| WO | 01 21213 A2 | 3/2001 |
| WO | WO 02/07759 A2 | 1/2002 |
| WO | WO 02/09743 A1 | 2/2002 |
| WO | WO 02/074327 A2 | 9/2002 |
| WO | WO 02/074327 A3 | 9/2002 |

OTHER PUBLICATIONS

Johnson (Neurotoxigenic Clostridia. In: Fischetti, V.A. (EDS) Gram-Positive Pathogens. ASM Press, Washington, DC. pp. 539-550).*
Hatheway (Clinical Microbiology Reviews 3(1): 66-98, Jan. 1990).*
Gura. Systems for Identifying New Drugs Are Often Faulty. Science 278: 1041 and 1042, Nov. 7, 1997.*
Bodey et al. Failure of Cancer Vaccines: The Significant Limitations of this Approach to Immunotherapy. Anticancer Research 20: 2665-2676, 2000.*
Chamberlain and Kaufman. Innovations and stategies for the development of anticancer vaccines. Exp. Opin. Pharmacother. 14: 603-614, 2000.*
Wald and Kakulas. Apocrine gland carcinoma (sweat gland carcinoma) of the breast. The Australian and New Zealand Journal of Surgery 33(3): 200-201, Feb. 1964.*
Richards, A., et al., *Plastic and Reconstructive Surgery*, Jul. 2001 pp. 270-271, "Botox for contraction of pectoralmuscles".
Schwartz, M.S., et al., *Movement Disorders*, vol. 13, No. 1, 1998, pp. 188-190, "Neuromyotonia in a muscle flap producing a convulsing breast: successful treatment with botulinum toxin".
Senior, M.A., et al., *Plastic and Reconstructive Surgery*, Jul. 2000, pp. 224-225, "Botox and the management of pectoral spasm after subpectoral implant insertion".
Andersson, J., et al., *Differential sorting of SNAP-25a and SNAP-25b proteins in neuroblastoma cells*, European Journal of Cell Biology 79, 781-789 (Nov. 2000).
Bagshawe, K.D. et al., *Antibody directed enzyme prodrug therapy (ADEPT): Clinical Report*, Disease Markers, vol. 9, 233-238 (1991).

(Continued)

*Primary Examiner*—Alana M Harris
(74) *Attorney, Agent, or Firm*—Kenton Abel; Claude L. Nassif; Debra Condino

(57) ABSTRACT

A method for treating a mammary gland disorder, including hyperplastic, hypertonic, cystic and/or neoplastic mammary gland tissue by local administration of a botulinum toxin to or to the vicinity of the afflicted breast tissue.

9 Claims, No Drawings

OTHER PUBLICATIONS

Bagshawe, K.D., et al., *A cytotoxic agent can be generated selectively at cancer sites*, Br. J. Cancer (1988) 58. 700-703.

Balakina, G.B., et al. *Localization of Choline Acetyltransferase in the alveolar portio nof th emammary gland of the white mouse*, Arkh Anat Gistol Embriol Apr. 1986; 90(4): 73-77—Russian.

Bigalke, H., et al., *Botulinum A Neurotoxin Inhibits Non-Cholinergic Synaptic Transmission in Mouse Spinal Court Neurons in Culture*, Brain Research, 360 (1985) 318-324, Elsevier.

Bigalke, H., et al., *Tetanus Toxin and Botulinum A Toxin Inhibit Release and Uptake of Various Transmitters, as Studied with Particulate Preparations from Rat Brain and Spinal Cord*, Naunyn-Schmiedeberg's Arc Pharmacol (1981) 316:244-251.

Boyd, R.S., et al., *The Effect of Botulinum Neurotoxins on the Release of Insulni from the Insulinoma Cell Lines HIT-15 and RINm5F*, The American Society for Biochemistry and Molecular Biology, Inc., 18216-18218, Aug. 4, 1995, vol. 270, No. 31.

Bryan, M., *Glomus Tumors*, Dept. of Otolaryngology, UTMB, Jan. 11, 1995 10 pgs.

Cabello, G., et al., *A Rat Mammary Tumor Model Induced by the Organophosphorous Pesticides Parathion and Malathion, Possibly through Acetylcholinesterase Inhibition*, Environmental Health Perspectives, vol. 109 No. 5, May 2001.

Col, V., et al., *Heart Failure Induced by Pheochromocytoma: Laparoscopic Treatment and Intraoperative Changes of Several New Cardiovascular Hormones*, Hormone Research, 1999; 51:51-52.

Cukan, M., et al., *Expression of SNAP-23 and SNAP-25 in the Pancreatic Acinar Tumor Cell Line AR42J*, Molec Biol Cell 1999;20(Suppl):398a.

Der, R., et al., *Gastric Neoplasms*, Gastrointestinal Pathology, (1999) pp. 105-144.

Dorosevich, A.E., et al., *Autonomic Nerve Endings and Their Cell Microenvironment as one of the integral parts of the stromal component in breast dysplasia and cancer*, Arkh Patol Nov.-Dec. 1994;56(6):49-53—Russian.

Duggan, M.J., et al., *A survey of botulinum neurotoxin substrate expression in cells*, Mov Disord May 1995; 10(3):376.

Ellis, I.O., et al., *Tumors of the Breast*, Diagnostic Histopathology of Tumors, vol. 1, $2^{nd}$ ed. 2000, pp. 865-930.

Eccles, S.A., et al., *Regression of Established Breast Carcinoma Xenografts with Antibody-directed Enzyme Prodrug Therapy against C-erbB2 p185[1]* Cancer Research 54, 5171-5177, Oct. 1, 1994.

Fabian, C.J., et al., *Beyond Tamoxifen New Endpoints for Breast Cancer Chemoprevention, New Drugs for Breast Cancer Prevention*, Ann NY Acad Sci 2001; 952: 44-59.

Foran, P., et al., *Blockade by Botulinum Neurotoxin B of Catecholamine Release from Adrenochromaffin Cells Correlates with its Cleavage of Synaptobrevin and a Homologue Present on the Granules*, Biochemistry 1995, 34, 5494-5503.

Gil, A., et al., *Dual effects of botulinum neurotoxin A on the secretory stages of chromaffin cells*, European Journal of Neuroscience, vol. 10, pp. 3369-3378, 1998.

Goodall, Neuroblastoma A.R., et al., *Occurrence of Two Types of Secretory Vesicles I the Human Neuroblastoma SH-SY5Y*, Journal of Neurochemistry, vol. 68, No. 4, 197, pp. 1542-1552.

Graff, L., et al., *Expression of Vesicular Monamine Transporters, Synaptosomal-assocated Protein 25 and Syntaxin1 : a Signature of Huam Small Cell Lung Carcinoma*, Cancer Research 61, pp. 2138-2144, Mar. 1, 2001.

Grosse, J., et al., *Synaptosome-Associate Protein of 25 Kilodaltons in Oocytes and Steroid-Producing Cells of Rat and Human Ovary: Molecular Analysis and Regulation by Gonadotropins*, Biology of Reproduction 63, 643-650 (2000).

Habermann, E., et al., *Tetanus Toxin,and Botulinum A and C Neurotoxins Inhibit Noradrenaline Release from Cultured Mouse Brain*, Journal of Neurochemistry, vol. 51, No. 2, 1988.

Hallett, M., *One Man's Poison—Clinical Applications of Botulinum Toxin*, New England Journal of Medicine, Jul. 8, 1999, pp. 118-120.

Heppner, F., *New Technologies to Combat Malignant Tumours of the Brain*, Anticancer Research, 2: 101-110 (1982).

Heppner, F., et al., *The Liquefaction (Oncolysis) of Malignant Gliomas by a Non Pathogenic Clostridium*, ACTA Neurochirurgica 42, (1978) pp. 123-125.

Huang, X., et al., *Truncated SNAP-25 (1-197), Like Botulinum Neurotoxin A, Can Inhibit Insulin Secretion from HIT-T15 Insulinoma Cells*, Molecular Endocrinology, 1998, vol. 12 No. 7, pp. 1060-1070.

Jankovic, J., et al., editors, *Therapy with Botulinum Toxin*, Marcel Dekker, Inc., publisher; p. 45 (1994).

Johnson, R K., et al., *The clinical impact of screening and other experimental tumor studies*, Cancer Treatment Reviews (1975) 2, pp. 1-31.

John, H., et al., *Pheochromocytomas: can malignant potential be predicted?*, Elsevier Science, Inc. Urology 53 (4), 1999, pp. 679-683.

Laskawi, R., *Up-to-date Report of Botulinum Toxin Type A Treatment in Patients With Gustatory Sweating (Frey's Syndrome)*, Laryngoscope 108: Mar. 1998, pp. 381-384.

Lemmon, M.J., et al., *Anaerobic bacteria as a gene delivery system to tumors*, Proceedings of the American Association for Cancer Research, #2231, Experimental Therapeutics, p. 374, vol. 35, Mar. 1994.

Lin, J.C., et al., *Cardiac Pheochromocytoma: Resection after Diagnosis by 111-Indium Octreotide Scan*, Ann Thorac Surg 1999; 67:555-8.

Majo, G., et al., *Immunocytochemical Analysis of the Synaptic Proteins SNAP-25 and Rab3A in Human Pituitary Adenomas. Overexpression of Snap-25 in the Mammosomatotroph Lineages*, Journal of Pathology, vol. 183: 440-446 (1997).

Maksymowych, A.B., et al., *Binding and Transcytosis of Botulinum Neurotoxin by Polarized Human Colon Carcinoma Cells*, The Journal of Biological Chemistry, vol. 273, No. 34 Aug. 21, pp. 21950-21957, 1998.

Meyer, K.E., *A Comparative Systemic Toxicity Study of Neurobloc in Adult and Juvenile Cynomolgus Monkeys*, Mov Disord 2000:15 (Suppl 2):54.

Sivridis, E., et al., *Prognostic aspects on endometrial hyperplasia and neoplasia*, Virchows Arch (2001) 439:118-126.

Springer, C.J., et al., *Ablation of Human Choriocarcinoma Xenofrafts in Nude Mide by Antibody-directed Enzyme Prodrug Therapy (ADEPT) with Three Novel Compounds*, Eur J Cancer, vol. 27, No. 11, pp. 1361-1366, 1991.

Sunaga, H., et al., *Expression Of Granulocyte Colony-Stimulating Factor Receptor and Platelet-derived Endothelial Cell Growth Factor in Oral and Oropharyngeal Precancerous Lesions*, Anticancer Research 21:2901-2906 (2001).

Van Poppel, H., et al.,*Precancerous Lesions in the Kidney*, Scand J Urol Nephrol Suppl 2000, (205), pp. 136-165.

Walther, M.M., et al., *Pheochromocytoma: evaluation, diagnosis, and treatment*, World J Urol (1999) 17: 35-39.

Warwar, R.E., et al., *Coexistence of 3 Tumors of Neural Crest Origin*, Arch Ophthalmol, vol. 116, Sep. 1998, pp. 1241-1243.

Williamson, L.C., et al., *Clostridial Neurotoxins and Substrate Proteolysis in Intact Neurons*, The Journal of Biological Chemistry, vol. 271, No. 13, Mar. 29, 1996, pp. 7694-7699.

Xu, T., et al., *Kinetic Studies of $Ca^{2+}$ Binding and $Ca^{2+}$ Clearance in the cytosol of Adrenal Chromaffin Cells*, Biophysical Journal, vol. 73, Jul. 1997, pp. 532-545.

Zimmerman, U.P., et al., *Proteolysis of Syunaptobrevin, Syntaxin, and Snap-25 in Alveolar Epithelial Type II Cells*, IUBMB Life, 48:453-458, 1999.

\* cited by examiner

METHODS FOR BREAST TREATMENT

CROSS REFERENCE

This application is a divisional of application Ser. No. 10/071,826, filed Feb. 8, 2002, which is a continuation in part of application Ser. No. 09/631,221, filed Aug. 2, 2000 now abandoned, which is a continuation in part of application Ser. No. 09/454,842, filed Dec. 7, 1999, now U.S. Pat. No. 6,139,845.

BACKGROUND

The present invention relates to methods for treating atypical tissues, such as hyperplastic tissues, cysts and neoplasms (including tumors and cancers) and for preventing the development of, or for causing the regression or remission of, atypical tissues, cysts and neoplasms. In particular, the present invention relates to methods for treating mammary gland disorders, such as mammary gland cysts and neoplasms, both benign and cancerous, as well as for treating hyperplastic and/or hypertonic mammary gland cells by local administration of a Clostridial toxin to or to the vicinity of the afflicted mammary gland tissue.

It is known that many hyperplastic tissues can, if not treated, develop into cancerous tissues, for example (1) different hyperplasia, metaplasic or atypical breast tissues can develop into cancers (see e.g. Ellis I. O., et al, *Tumors of the Breast*, chapter 16 (pages 865-930) of "Diagnostic Histopathology of Tumors", volume 1, edited by Fletcher C. D. M., second edition, Churchill Livingstone (2000), discussed further infra, as well as Fabian C. J. et al *Beyond tamoxifen new endpoints for breast cancer chemoprevention, new drugs for breast cancer prevention*, Ann NY Acad Sci 2001 December; 952:44-59); (2) hyperplastic intestinal tissues, such as polyps can transform into carcinomas (see e.g. Der, R. et al *Gastric Neoplasms*, chapter 5 (pages 105-144) of Chandraspma, P., "Gastrointestinal Pathology", Appleton & Lange (1999), in particular pages 106-107; (3) oral and oropharyngeal epithelial hyperplasia indicates a precancerous lesion. Sunaga H., et al. *Expression of granulocyte colony-stimulating factor receptor and platelet-derived endothelial cell growth factor in oral and oropharyngeal precancerous lesions*. Anticancer Res 2001 July-August; 21(4B):2901-6; (4) Endometrial hyperplastic tissue is a precancerous tissue. Spyridis E. et al., *Prognostic aspects on endometrial hyperplasia and neoplasia*, Virchows Arch 2001 August; 439(2):118-26, and; (5) kidney and prostate cell hyperplasia has been documented as a factor leading to development of cancerous cells. Van Poppel, H., et al., *Precancerous lesions in the kidney* Scand J Urol Nephrol Suppl 2000; (205):136-65

The breasts (synonymously, mammary glands) of the human female are highly modified apocrine sweat glands with the specialized function of providing nutrients to the newborn infant. The breast consists of epithelial glandular tissue of the tubuol-alveolar type, fibrous connective tissue (stroma) surrounding the glandular tissue and interlobar adipose tissue. The nerve supply of the breast is derived from the anterior and lateral branches of the fourth to sixth intercostal nerves which carry sensory and sympathetic efferent fibers. Secretory activities of the glandular tissue are controlled largely by ovarian and hypophyseal hormones rather than by efferent motor fibers. In the female, breasts develop at puberty and regress at menopause. During pregnancy, the secretory components in the breast expand greatly in size and number in preparation for lactation. Each breast consists of 15-25 independent glandular units called breast lobes, each consisting of a compound tubulo-acinalar gland. Each lobe leads to a lactiferous duct which converges with the others upon the nipple. The lobes are embedded in a mass of adipose tissue which is subdivided by collagenous septa. A specialized area of skin, the areola surrounds the base of the nipple. The breast lies upon the deep pectoral fascia, which in turn overlies the pectoral muscle and the serratus anterior muscle.

Breast cancer is the most common cancer in women (excluding skin and lung cancer) and in the United States in 1999, over 175,000 women were diagnosed with breast cancer and it is estimated that of this number approximately 43,300 will die from the disease. Breast cancer kills about 40,000 woman every year in the United States. In the United States, breast cancer accounts for 29% of all cancers in women. It has been estimated that one woman out of eight will develop breast cancer sometime during her life. Although early detection results in higher cure rates, breast cancer remains the leading cause of cancer death of adult women under 54 years of age and the second most common cause after age 54. Among women of all ages, breast cancer is second only to lung cancer as the leading cause of cancer death in women. Less than 1% of all breast cancer cases occur in men.

Benign breast tumors can include fibrocystic change, fibroademoma and variants, sclerosing lesions, papilloma (a structure composed of fibrovascular cores covered by epithelium) and proliferative breast disease. Cysts are believed to arise from a process of lobular involution. A cyst is a pathologically dilated sac lined by epithelium and containing fluid. Two main forms of breast cyst are recognized, cysts lined by a layer of epithelium and the more common form of cyst which is lined with apocrine-type epithelium, which resembles normal apocrine sweat gland epithelium. Cysts are believed to arise from a process of lobular involution and are very common, occurring in about 19% of the general population and are palpable in 7%. Management is usually by aspiration. Cysts can be found in about 77% of cancer-bearing breasts (Ellis et al, page 866). The apocrine epithelial layer of a breast cyst can show hyperplasia. Additionally, apocrine metaplasia is a frequent finding in the breast and is generally associated with cyst formation. Furthermore, apocrine metaplasia can be associated with other, noncystic, benign mammary gland afflictions, including sclerosing adenosis (adenosis is an increased number or enlargement of glandular components), papillomas and fibroadenomas. Significantly, apocrine change (atypia), which is not an inflammatory disorder, is regarded as indicating as a type of precancerous tissue which presents for the patient a significantly increased risk of subsequent development of breast carcinoma, such as apocrine carcinoma or medullary carcinoma. Finally, epithelial hyperplasia, ductal hyperplasia and lobular hyperplasia are all also regarded as a precancerous breast tissue condition which all point to a risk of developing breast cancer. Ellis I. O., et al, *Tumors of the Breast*, supra, in particular pages, 866-867, 881 and 884.

Thus, it is clear that benign proliferative or fibrocystic changes (fibrocystic disease), as well as hyperplasia, have been identified as morphologic markers of risk for the development of breast carcinoma. Rosen, P. R., *Rosen's Breast Pathology*, second edition, Lippincott Williams & Wilkins (2001), chapter 10 ("Precancerous Breast Disease"), pages 229-248, in particular pages 231-232 and 236-239.

Gene mutations account for approximately 5% of the familial breast cancer. Li-Fraumeni syndrome is a rare hereditary syndrome associated with an increased incidence of breast, brain, and adrenal neoplasms, as well as sarcomas, lymphomas, and leukemias. The cause of this syndrome is believed to be associated with mutation of the p53 gene, which is a tumor suppressor gene.

Breast cancer can be characterized as a malignant proliferation of epithelial cells lining the ducts or lobules of the breast. It is generally believed that breast cancer is hormone dependant, since women without functioning ovaries and who never receive estrogen replacement apparently do not typically develop breast cancer. Malignant tumors may arise from any of the breast structures. Ductal carcinomas are the most common ones, followed by lobular carcinomas, and malignancies arising from other connective tissues.

Invasive (infiltrating) ductal carcinoma is the most common cell type, comprising 70% to 80% of all cases of breast cancer. The tumors occur throughout the age range of breast carcinoma, being most common in women in their middle to late 50 s. It is characterized by its solid core, which is usually hard and firm on palpation. An associated ductal carcinoma in-situ is frequently present and comedo necrosis may occur in both invasive areas and areas of intraductal carcinoma. Invasive ductal carcinoma commonly spreads to the regional lymph nodes and carries the poorest prognosis among various ductal types. Nuclear and histologic grade have shown to be effective predictors of prognosis.

Ductal carcinoma in-situ (DCIS) consists of malignant epithelial cells confined to the mammary ducts, without microscopic evidence of invasion through the basement membrane into the surrounding tissue. According to the tumor differentiation, DCIS can be further divided into low, intermediate, and high grade. Such stratification has prognostic implications. There are five histologic subtypes of DCIS, namely comedo, papillary, micropapillary, cribriform, and solid. The comedo subtype carries the higher probability of high nuclear grade, microinvasion, and over expression of the her-2/neu oncogene. The most characteristic mammographic abnormality associated with DCIS is "clustered microcalcifications". New classification systems using a combination of architecture, nuclear grade, and necrosis have been proposed. Invasive lobular carcinoma is relatively uncommon, comprising only 5% to 10% of breast tumors. Invasive lobular carcinomas are characterized by greater proportion of multicentricity in the same or the opposite breast. The lesions tend to have ill-defined margins, and occasionally the only evidence is subtle thickening or induration. Patients with infiltrating lobular carcinoma are especially prone to have bilateral carcinoma. Stage by stage, invasive lobular carcinoma has a similar prognosis to infiltrating ductal carcinoma.

Lobular carcinoma in-situ (LCIS) generally lacks specific clinical or mammographic signs, and occurs more frequently in premenopausal women. By definition, these cancer cells are confined to the mammary lobules without invasion. LCIS is characterized microscopically by a solid proliferation of small cells. The cells have a low proliferative rate, are typically estrogen receptor positive, and rarely over express the her-2/neu oncogene. Since there is a reported risk of bilaterally in this disease, some investigators have recommended treatment with bilateral simple mastectomy with immediate breast reconstruction. If watchful waiting is elected, lifetime observation is mandatory since the increased risk of breast cancer persists indefinitely. Tubular carcinoma is also known as a well-differentiated carcinoma. The frequency of axillary lymph node metastases is approximately 10%, lower than that of ductal carcinoma. The prognosis is considerably better than for invasive ductal carcinoma. Medullary carcinoma is characterized by a prominent lymphocyte infiltrate. Patients with medullary carcinoma tend to be younger than those with other types of breast cancer. The prognosis is also believed to be better than for invasive ductal cancer.

Inflammatory breast carcinoma is characterized by diffuse skin edema, skin and breast redness, and firmness of the underlying tissue without a palpable mass. The clinical manifestation is primarily due to tumor embolization to dermal lymphatics (skin lymph channels) with associated engorgement of superficial capillaries. Inflammatory breast cancer carries a poor prognosis and is preferably treated by excision.

Paget's disease of the nipple is a rare form of breast cancer that is characterized clinically by eczematoid changes of the nipple. It is believed that Paget's disease represents the migration of malignant cells from subjacent mammary ducts in the nipple. The prognosis of patients with Paget's disease appears to be similar to that of women with other types of breast carcinoma, stage for stage.

Benign breast tumors include fibroademoma, periductal fibromas (a connective tissue tumor), intraductal epithelial tumor, retention cysts, lipomas (fatty tumor), chronic cystic mastitis and fat necrosis. Most often they occur during the reproductive period of life or just after. These are often difficult to distinguish from malignant tumors and must be watched for a change in size, or lymphatic involvement, in which case the growth should be cut out and examined. Mammograms, ultrasound, thermography and aspiration of cystic forms can aid in diagnosis.

A diagnosis of breast cancer can be made by a pathological examination of breast tissue. A lump in the breast usually warrants biopsy even when the mammogram is described as being normal. Breast tissue can be obtained by needle aspiration biopsy or surgical biopsy. Needle aspiration is used by some physicians to help differentiate between cysts and solid tumors. Cysts frequently disappear after aspiration and the removal of fluid. Cytological or pathological examinations of material removed in the aspiration can be used to identify the cancer. Ultrasound can help determine whether the lump is solid or cystic. Breast MRI can also be used. Excisional biopsy, the most commonly performed procedure, is used when lumps are small. In these cases, the entire tumor and a margin of normal tissue are excised. If the tumor is large, incisional biopsy may be done to remove a small amount of tissue for pathological examination. Tissue obtained from surgical biopsy can be evaluated by frozen section, which permits a diagnosis within 30 minutes and may be followed by definitive surgery; but most surgeons wait for a permanent section, which take about 24-48 hours. The latter approach is allows the patient time to discuss treatment options with the physician and is the more common approach.

The most common route of spread of breast cancer is to the axillary lymph nodes. About 30-40% of breast cancer patients already have positive (disease-affected) axillary nodes when the tumor is palpable. The more axillary nodes that are involved, the greater the risk of micrometastases (clinically undetectable tumor cells) elsewhere and relapse or recurrence. The common sites of breast cancer recurrence are local recurrence at the original site in the breast or distant spread to bone, liver, lung, and brain. Some complications of metastatic disease include spinal cord compression, pathological bone fractures, pleural effusion, and bronchial obstruction.

Breast cancers are dividing according to the cell type, with types varying with incidence, patterns of growth and metastases, and survival. Infiltrating ductal carcinoma is the most common type of breast cancer, accounting for about 70% of the tumors. The rare inflammatory breast cancers (1-4% of breast cancer cases) are associated with the poorest prognosis. Carcinoma in situ (CIS) is a non-invasive cancer that has an excellent prognosis and can often be detected by mammography when nothing significant is palpable.

Treatment recommendations differ depending on the type and stage of disease at the time of diagnosis. Stage I or II disease is generally treated by breast conservation surgery and irradiation, or modified radical mastectomy with or without breast reconstruction. Mastectomy and irradiation are local treatments and obviously will not affect cancer cells that have already metastasized. Adjuvant chemotherapy may also be given to patients with early-stage disease who are at a higher risk for developing metastatic disease. For patients with positive estrogen receptors, adjuvant chemotherapy or tamoxifen are now considered a standard treatment. The role of ovarian ablation of suppression for premenopausal ER-positive patients is under clinical investigation. A sentinal lymph node is the first lymph node along the route of lymphatic drainage from a primary tumor. Sentinel lymph node biopsy following injection of radio-isotope (technetium-99m sulfur colloid) and/or vital blue dye around the primary tumor or tumor bed carries lower morbidity and cost than a complete axillary dissection. This technique remains under investigation. Patients with locally advanced breast cancers (Stage III) have a poorer prognosis. Good local control may be achieved with a combination of surgery, chemotherapy, and irradiation. Chemotherapy is considered because patients with stage III disease are at risk for developing distant metastases. Treatment approaches for patients with locally recurrent or metastatic disease vary depending on the site and extent of disease. In many cases, local and systemic therapies are combined. Because patients with metastatic disease rarely exhibit a lasting response to standard treatments, researchers are evaluating the use of high-dose chemotherapy regimens followed by autologous bone marrow transplant (or stem cell replacement).

Breast conservation surgery consists of excision of the tumor and a partial (lower) axillary lymph node dissection. The terms "lumpectomy," "segmental resection", "tylectomy", and "partial mastectomy" are frequently used to describe the local surgery. Surgery is typically followed by radiation therapy for all the patients with invasive carcinoma and majority of patients with carcinoma in-situ. Recent studies of patients with small tumors up to 5 cm (about 2 inches) in size and no evidence of multifocal disease or extensive intraductal cancer show no difference in survival between breast conservation surgery followed by radiation therapy and modified radical mastectomy. Modified radical mastectomy is a removal of the entire breast plus an axillary node dissection. The disadvantages of a modified radical mastectomy are cosmetic deformity and the potential for psychosocial problems affecting body image and self-concept.

There are many deficiencies and drawbacks of the current therapies for benign breast affliction and breast cancers. Thus modified radical mastectomy results in loss of body part, altered body image, need for a prosthesis, optional reconstructive surgery, chest wall tightness and skin flap necrosis. Partial mastectomy results in axillary node dissection and irradiation, breast fibrosis, hyperpigmentation, rib fractures, breast edema, changes in the skin sensitivity, myositis and prolonged duration of primary therapy. Indeed both radical and partial mastectomy can result in sensory loss, a need for hand and arm care and post-operative complications which can include seroma, hematoma, wound infection, lymphedema, arm weakness, pain, psychological distress, impaired arm mobility, nerve injury and fatigue. A seroma is the accumulation of serous or serosanguinous fluid in the dead space of the axillary fossa or chest wall. Seromas can delay healing and foster infection. Hematomas occur when blood accumulates in the interstitial space and can be aspirated when liquefied or be reabsorbed over time without intervention.

Nerve injury may occur despite surgical efforts to avoid trauma. Patients may complain of sensations of pain, tingling, numbness, heaviness, or increased skin sensitivity on the arm or chest. These sensations change over time and usually disappear during or after one year. Less often, muscle atrophy may occur secondary to nerve injury and result in decreased arm or shoulder function.

Since clinically undetectable breast cancer cells may be left following local excision of the cancer, radiation therapy is given for local tumor control. Radiation therapy can also be used preoperatively to shrink large breast tumors and make them more easily resectable. Palliative radiation therapy is commonly used to relieve the pain of bone metastasis and for the symptomatic management of metastases to other sites, such as the brain. Fatigue, skin reactions, changes in sensation, color and texture of the skin, and breast swelling are common during and immediately following a course of radiation therapy to the breast.

Chemotherapy, hormone therapy, or a combination of the two can be used to palliate the effects of metastatic disease. Recommendations for adjuvant chemotherapy and/or adjuvant hormone therapy are usually based on the number of positive axillary nodes, menopausal status, size of the primary tumor, and the estrogen receptor assay. The chemotherapeutic drugs most commonly used are alkylating agents, antimetabolites, antitumor antibiotics (Herceptin) and vinca alkaloids. Hormone manipulation is achieved primarily through hormone blockers and infrequently by surgical removal of sex hormone-producing glands (oophorectomy, adrenalectomy, or hypophysectomy). Tamoxifen, an anti-estrogen, is the most widely used hormonal agent. The second-line hormonal agents, such as Femara, and Arimidex, are now available for ER/PR negative patients and/or patients who failed tamoxifen. Unfortunately, chemotherapy for breast cancer can have numerous deleterious side effects including fatigue, weight gain, nausea, vomiting, alopecia, disturbances in appetite and taste, neuropathies, diarrhea, bone marrow suppression, menopausal symptoms, hair loss and weight gain. Additionally, the first line drug of choice, tamoxifen, can increase the risk of uterine cancer and blood clots.

Botulinum Toxin

The anaerobic, gram positive bacterium *Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of botulinum toxin (purified neurotoxin complex) type $A^1$ is a $LD_{50}$ in mice. One unit (U) of botulinum toxin is defined as the $LD_{50}$ upon intraperitoneal injection into female Swiss Webster mice weighing 18-20 grams each. Seven immunologically distinct botulinum neurotoxins have been characterized, these being respectively botulinum neurotoxin serotypes A, B, $C_1$, D, E, F and G each of which is distinguished by neutralization with type-specific antibodies. The different serotypes of botulinum toxin vary in the animal species that they affect and in the severity and duration of the paralysis they ev example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. Botulinum toxin apparently binds with high affinity to cholinergic motor neurons, is translocated into the neuron and blocks the release of acetylcholine.

[1]Available from Allergan, Inc., of Irvine, Calif. under the tradename BOTOX®.

Botulinum toxins have been used in clinical settings for the treatment of neuromuscular disorders characterized by hyperactive skeletal muscles. Botulinum toxin type A has been approved by the U.S. Food and Drug Administration for the treatment of blepharospasm, strabismus, hemifacial spasm and cervical dystonia. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes.

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$ is apparently produced as only a 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP and glutamate.

Botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

It has been reported that botulinum toxin type A has been used in clinical settings as follows:

(1) about 75-250 units of BOTOX® per intramuscular injection (multiple muscles) to treat cervical dystonia;

(2) 5-10 units of BOTOX® per intramuscular injection to treat glabellar lines (brow furrows) (5 units injected intramuscularly into the procerus muscle and 10 units injected intramuscularly into each corrugator supercilii muscle);

(3) about 30-80 units of BOTOX® to treat constipation by intrasphincter injection of the puborectalis muscle;

(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:

(a) flexor digitorum profundus: 7.5 U to 30 U (b) flexor digitorum sublimus: 7.5 U to 30 U (c) flexor carpi ulnaris: 10 U to 40 U (d) flexor carpi radialis: 15 U to 60 U (e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

The success of botulinum toxin type A to treat a variety of clinical conditions has led to interest in other botulinum toxin serotypes. A study of two commercially available botulinum type A preparations (BOTOX® and Dysport®) and preparations of botulinum toxins type B and F (both obtained from Wako Chemicals, Japan) has been carried out to determine local muscle weakening efficacy, safety and antigenic potential. Botulinum toxin preparations were injected into the head of the right gastrocnemius muscle (0.5 to 200.0 units/kg) and muscle weakness was assessed using the mouse digit abduction scoring assay (DAS). $ED_{50}$ values were calculated from dose response curves. Additional mice were given intramuscular injections to determine $LD_{50}$ doses. The therapeutic index was calculated as $LD_{50}/ED_{50}$. Separate groups of mice received hind limb injections of BOTOX® (5.0 to 10.0 units/kg) or botulinum toxin type B (50.0 to 400.0 units/kg), and were tested for muscle weakness and increased water consumption, the later being a putative model for dry mouth. Antigenic potential was assessed by monthly intramuscular injections in rabbits (1.5 or 6.5 ng/kg for botulinum toxin type B or 0.15 ng/kg for BOTOX®). Peak muscle weakness and duration were dose related for all serotypes. Water consumption was greater in mice injected with botulinum toxin type B than with BOTOX®, although botulinum toxin type B was less effective at weakening muscles. After four months of injections 2 of 4 (where treated with 1.5 ng/kg) and 4 of 4 (where treated with 6.5 ng/kg) rabbits developed antibodies against botulinum toxin type B. In a separate study, 0 of 9 BOTOX® treated rabbits demonstrated antibodies against botulinum toxin type A. DAS results indicate relative peak potencies of botulinum toxin type A being equal to botulinum toxin type F, and botulinum toxin type F being greater than botulinum toxin type B. With regard to duration of effect, botulinum toxin type A was greater than botulinum toxin type B, and botulinum toxin type B duration of effect was greater than botulinum toxin type F. As shown by the therapeutic index values, the two commercial preparations of botulinum toxin type A (BOTOX® and Dysport®) are different. The increased water consumption behavior observed following hind limb injection of botulinum toxin type B indicates that clinically significant amounts of this serotype entered the murine systemic circulation. The results also indicate that in order to achieve efficacy comparable to botulinum toxin type A, it is necessary to increase doses of the other serotypes examined. Increased dosage can comprise safety. Furthermore, in rabbits, type B was more antigenic than as BOTOX®, possibly because of the higher protein load injected to achieve an effective dose of botulinum toxin type B.

It is known to use a botulinum toxin to treat: intrathecal pain (see e.g. U.S. Pat. No. 6,113,915); paragangliomas (see e.g. U.S. Pat. No. 6,139,845); otic disorders (see e.g. U.S. Pat. No. 6,265,379); pancreatic disorders (see e.g. U.S. Pat. Nos. 6,143,306 and 6,261,572); migraine (see e.g. U.S. Pat. No. 5,714,468); smooth muscle disorders (see e.g. U.S. Pat. No. 5,437,291); prostate disorders, including prostatic hyperplasia (see e.g. WO 99/03483 and Doggweiler R., et al *Botulinum toxin type A causes diffuse and highly selective atrophy of rat prostate*, Neurourol Urodyn 1998; 17(4):363); autonomic nerve disorders, including hyperplastic sweat glands (see e.g. U.S. Pat. No. 5,766,606); wound healing (see e.g. WO 00/24419); reduced hair loss (see e.g. WO 00/62746); skin lesions (see e.g. U.S. Pat. No. 5,670,484), and; neurogenic inflammatory disorders (see e.g. U.S. Pat. No. 6,063,768). U.S. Pat. No. 6,063,768 cursorily discloses at column 6 lines 39-42 treatment of the inflammatory joint condition pigmented villonodular synovitis and a particular type of joint cancer, synovial cell sarcoma. Column 6, line 53 of U.S. Pat. No. 6,063,768 also discloses, without further explanation, that "tumors" can be treated.

Additionally it has been disclosed that targeted botulinum toxins (i.e. with a non-native binding moiety) can be used to treat various conditions (see e.g. U.S. Pat. No. 5,989,545, as well as WO 96/33273; WO 99/17806; WO 98/07864; WO 00/57897; WO 01/21213; WO 00/10598.

A botulinum toxin has been injected into the pectoral muscle to control pectoral spasm. See e.g. Senior M., *Botox and the management of pectoral spasm after subpectoral implant insertion*, Plastic and Recon Surg, July 2000, 224-225.

Both liquid stable formulations and pure botulinum toxin formulations have been disclosed (see e.g. WO 00/15245 and WO 74703) as well as topical application of a botulinum toxin (see e.g. DE 198 52 981).

Acetylcholine

Typically or in general, only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic and most of the postganglionic neurons of the sympathetic nervous system secrete the neurotransmitter norepinephrine. In most instances acetylcholine has an excitatory effect. However, acetylcholine is known to have inhibitory effects at some of the peripheral parasympathetic nerve endings, such as inhibition of the heart by the vagus nerves.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic neurons of the parasympathetic nervous system, as well as in those stimulated by the postganglionic cholinergic neurons of the sympathetic nervous system. The nicotinic receptors are found in the synapses between the preganglionic and postganglionic neurons of both the sympathetic and parasympathetic. The nicotinic receptors are also present in many membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and insulin, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

Wide Distribution of the Botulinum Toxin Substrate

It is known that a botulinum toxin can denervate muscle cells resulting in a flaccid paralysis due to a presynaptic inhibition of acetylcholine release from neurons at a neuromuscular junction. The proteolytic domain of a botulinum toxins acts upon a particular substrate in the cytosol of target cells, cleavage of the substrate preventing membrane docking and exocytosis of acetylcholine containing secretory vesicles. The absence of acetylcholine in the synaptic cleft between innervating neuron and muscle cell prevents stimulation of the muscle cells and paralysis thereby results.

The botulinum toxins are intracellular proteases that act specifically on one or more of three different proteins which control the docking of acetylcholine to containing secretory vesicles. These specific substrates for the botulinum toxins are synaptobrevin, syntaxin and/or SNAP-25. See e.g. Duggan M. J., et al., *A survey of botulinum neurotoxin substrate expression in cells*, Mov Disorder 10(3); 376:1995, and Blasi J., et al., *Botulinum neurotoxin A selectively cleaves the synaptic protein SNAP-25*. Nature 365; 160-163:1993. For botulinum toxin types B, D, F and G the particular intracellular substrate is synaptobrevin. SNAP-25, synaptobrevin and syntaxin are known as SNAREs (soluble N-ethylmaleimide sensitive factor attachment protein receptors).

Significantly, it is not only the nerves which innervate muscles which contain the substrate for the botulinum toxins: "The presence of SNAP-25 in presynaptic regions of numerous neuronal subsets and in neural crest cell lines suggests that this protein subserves an important function in neuronal tissues." Oyler G. A. et al., *Distribution and expression of SNAP-25 immunoreactivity in rat brain, rat PC-12 cells and human SMS-KCNR neuroblastoma cells*, Brain Res Dev Brain Res 1992 Feb. 21; 65(2):133-146, 1992.

Additionally, "[T]he wide occurrence of the SNARE proteins in endocrine cells suggests that they may also serve as general diagnostic markers for endocrine tumors.", Graff, L., et al. *Expression of vesicular monoamine transporters, synaptosomal-associated protein 25 and syntaxin1: a signature of human small cell lung carcinoma*, Cancer Research 61, 2138-2144, Mar. 1, 2001, at page 2138. For example, it is known that SNAP-25 is widely distributed in neuroendocrine cells (including in chromaffin cells, PC12, GH3, and insulinomas). Furthermore, the botulinum toxin substrate synaptobrevin has been found in fibroblasts and myeloid cells (e.g. mast cells). Duggan M., et al., supra.

Indeed, SNAREs apparently influence or control the membrane fusion of secretory vesicles in most if not all secretory cells. Andersson J., et al, *Differential sorting of SNAP-25a and SNAP-25b proteins in neuroblastoma cells*, Eur J. Cell Bio 79, 781-789:November 2000.

Thus, the substrate for a botulinum toxin are not restricted to neuronal cells which release the neurotransmitter acetylcholine. The botulinum toxin substrates are therefore "ubiquitously involved in membrane-membrane fusion events" and the evidence points to "a universal mechanism for membrane fusion events" (i.e. for the docking of secretory vesicles with the cell wall) (Duggan 1995, supra).

Thus, the intracellular substrate for botulinum toxin has a ubiquitous distribution in both neuronal and non-neuronal secretory cells. This is clearly illustrated by discovery of the presence of SNAP-25 (a 25 kiloDalton synaptosomal-associated protein and substrate for at least botulinum toxin type A) in at least:

(1) the pancreas (Sadoul K., et al., *SNAP-25 is expressed in islets of Langerhans and is involved in insulin release*, J. Cell Biology 128; 1019-1029:1995;

(2) the hypophysis (Dayanithi G., et al. *Release of vasopressin from isolated permeabilized neurosecretory nerve terminals is blocked by the light chain of botulinum A toxin*, Neuroscience 1990; 39(3):711-5);

(3) the adrenal medulla (Lawrence G., et al. *Distinct exocytotic responses of intact and permeabilized chromaffin cells after cleavage of the 25-kDa synaptosomal associated protein (SNAP-25) or synaptobrevin by botulinum toxin A or B*, Eur J. Biochem 236; 877-886:1996);

(4) gastric cells (Hohne-Zell B., et al., *Functional importance of synaptobrevin and SNAP-25 during exocytosis of histamine by rat gastric enterochromaffin-like cells*, Endocrinology 138; 5518-5526:1997;

(5) lung tumors (Graff, L., et al. *Expression of vesicular monoamine transporters, synaptosomal-associated protein 25 and syntaxin 1: a signature of human small cell lung carcinoma*, Cancer Research 61, 2138-2144, Mar. 1, 2001 (small cell lung carcinomas (SCLCs) contain SNAP-25);

(6) intestinal tumors, Maksymowych A., et al., *Binding and transcytosis of botulinum neurotoxin by polarized human colon carcinoma cells*, J of Bio. Chem., 273 (34); 21950-21957: 1998 (botulinum toxin is internalized by human colon cancer cells);

(7) pancreatic tumors, Huang, X., et al., Truncated SNAP-25 (1-197), like botulinum neurotoxin A, can inhibit insulin secretion from HIT-T15 insulinoma cells, Mol. Endo. 12(7); 1060-1070:1998 (" . . . functional SNAP-25 proteins are required for insulin secretion . . . ", ibid. at page 1060). See also Boyd R., et al., *The effect of botulinum neurotoxins on the release of insulin from the insulinoma cell lines HIT-15 and RINm5F*, J. Bio Chem. 270(31); 18216-18218:1995, and; Cukan M., et al., *Expression of SNAP-23 and SNAP-25 in the pancreatic acinar tumor cell line AR42J*, Molec Biol Cell 20(suppl); 398a, no. 2305:1999 ("SNAP-25 is a SNARE protein that mediates exocytotic events in neuronal and endocrine systems.");

(8) pituitary tumors as well as in normal pituitary cells, Majo G., et al., *Immunocytochemical analysis of the synaptic proteins SNAP-25 and Rab3A in human pituitary adenomas. Overexpression of SNAP-25 in the mammososmatotroph lineages*, J. Pathol 1997 December; 183(4):440-446;

(9) neuroblastomas, Goodall, A., et al., *Occurrence of two types of secretory vesicles in the human neuroblastoma SH-SY5Y*, J. of Neurochem 68; 1542-1552:1997. See also Oyler, G. A, *Distribution and expression of SNAP-25 immunoreactivity in rat brain, rat PC-12 cells and human SMS-KCNR neuroblastoma cells*, Dev. Brain Res. 65 (1992); 133-146. Note that Goodall (1992) discusses only in vitro identification of certain vesicle docking proteins in a single neuroblastoma cell line;

(10) kidney cells (Shukla A., et al., *SNAP-25 associated Hrs-2 protein colocalizes with AQP2 in rat kidney collecting

*duct principal cells*, Am J Physiol Renal Physiol 2001 September; 281(3):F546-56 (SNAP-25 is involved in kidney cell "regulated exocytosis"), and;

(11) normal lung cells (Zimmerman U. J., et al., *Proteolysis of synaptobrevin, syntaxin, and SNAP-25 in alveolar epithelial type II cells*, IUBMB Life 1999 October; 48(4): 453-8), and; (12) all ovarian cells (Grosse J., et al., *Synaptosome associated protein of 25 kilodaltons in oocytes and steroid producing cells of rat and human ovary: molecular analysis and regulation by gonadotropins*, Biol Reprod 2000 August; 63(2): 643-50 (SNAP-25 found "in all oocytes and in steroidogenic cells, including granulosa cells (GC) of large antral follicles and luteal cells"

Cholinergic Mammary Gland Tissues

Diverse hyperplastic and neoplastic mammary gland cells are influenced by cholinergic mechanisms. Thus, it has been discovered that there is a "cholinergic mechanism in the alveolar cells activity". Balakina G. B., et al., *Localization of choline acetyltransferase in the alveolar portion of the mammary gland of the white mouse*, Arkh Anat Gistol Embriol 1986 April; 90(4):73-7. Additionally, there is cholinergic influence upon both mammary dysplasia (fibrocysts) and mammary carcinoma tissues (Dorosevich A. E., et al., *Autonomic nerve endings and their cell microenvironment as one of the integral parts of the stromal component in breast dysplasia and cancer*, Arkh Patol 1994 November-December; 56(6):49-53), as well as "a direct cholinergic stimulation of smooth muscle cells" in mammary arteries (Pesic S., et al., *Acetylcholine-induced contractions in the porcine internal mammary artery; possible role of muscarinic receptors*, Zentralbl Veterinarmed A 1999 October; 46(8): 509-15).

Significantly, an increase in acetylcholine due to inhibition of cholinesterase has been implicated in increase mammary cell proliferation followed by the development of mammary carcinomas. Cabello G., et al, *A rat mammary tumor model induced by the organophosphorous pesticides parathion and malathion, possibly through acetylcholinesterase inhibition*, Environ Health Perspect 2001 May; 109(5):471-9. Thus, a decrease in breast cancer cell proliferation appears to be mediated by a cholinergic mechanism. Panagiotou S., "*Opioid agonists modify breast cancer cell proliferation by blocking cells to the G2/M phase of the cycle: involvement of cytoskeletal elements*, J Cell Biochem 1999 May 1; 73(2): 204-11.

Adrenal Medulla

The adrenal or suprarenal glands are small, triangular-shaped structures located on top of the kidneys. Each adrenal gland comprises an adrenal cortex or outer portion and an adrenal medulla or inner portion. The cortex surrounds and encloses the medulla.

The adrenal cortex secretes the hormones cortisol and aldosterone. Cortisol is produced during times of stress, regulates sugar usage, and is essential for maintenance of normal blood pressure. Aldosterone is one of the main regulators of salt, potassium and water balance. If both adrenal glands are removed cortisol and aldosterone replacement therapy is mandatory.

The adrenal medulla secretes the catecholamines adrenalin (synonymously epinephrine) and noradrenalin (synonymously norepinephrine). These hormones are important for the normal regulation of a variety of bodily functions, including stress reaction, when they cause an increase in blood pressure, the pumping ability of the heart, and the level of blood sugar. Removal of the adrenal medulla results in little or no hormonal deficiency because other glands in the body can compensate. Contrarily, excessive catecholamine production can be life threatening.

In the normal adult male about 85% of total catecholamine made by the adrenal medulla is adrenaline, with the remaining 15% being noradrenalin. There is about 1.6 mg of catecholamine present per gram of medulla tissue. Most of the noradrenalin found in blood and urine comes not from the adrenal medulla but from postganglionic sympathetic nerve endings. If the freshly sectioned adrenal gland is placed in fixatives that contain potassium dichromate, the medulla turns brown and this is referred to as the chromaffin reaction, so named to suggest the affinity of adrenal medulla tissue for chromium salts. Hence, cells of the adrenal medulla are often called chromaffin cells. Chromaffin cells also exists outside the adrenal medulla, but usually secrete only noradrenalin, not adrenaline.

The adrenal medulla can be viewed as a sympathetic ganglion innervated by preganglionic cholinergic nerve fibers. These nerve fibers release acetylcholine which causes secretion of catecholamines (primarily adrenaline) by a process of exocytosis from the chromaffin cells of the adrenal medulla. The normal adrenal medulla is innervated by the splancnic nerve, a preganglionic, cholinergic branch of the sympathetic nervous system. The activity of the adrenal medulla is almost entirely under such cholinergic nervous control.

Chromaffin Cell Tumors

Chromaffin cells (including the chromaffin cells of the adrenal medulla) and sympathetic ganglion cells have much in common as they are both derived from a common embryonic ancestor, the sympathagonium of the neural crest, as shown diagrammatically below. Examples of the types of neoplasms which can arise from each these cell types is shown in brackets. Each of the cell types shown can potentially secrete catecholamines.

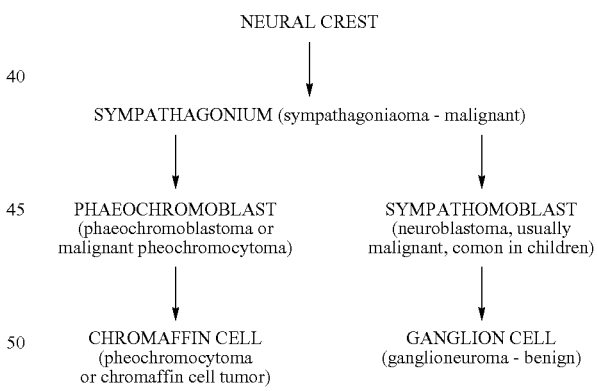

While most chromaffin cell neoplasms occur in the adrenal medulla, ectopic and multiple location chromaffin cell tumors are known, occurring most commonly in children.

1. Paragangliomas

A paraganglia (synonymously, chromaffin body) can be found in the heart, near the aorta, in the kidney, liver, gonads, and other places and is comprised of chromaffin cells which apparently originate from neural crest cells and which have migrated to a close association with autonomic nervous system ganglion cells. A paraganglioma is a neoplasm comprised of chromaffin cells derived from a paraganglia. A carotid body paraganglioma is referred to as a carotid paraganglioma, while an adrenal medulla paraganglioma is called a pheochromocytoma or a chromaffinoma.

The carotid body is often observed as a round, reddish-brown to tan structure found in the adventitia of the common carotid artery. It can be located on the posteromedial wall of the vessel at its bifurcation and is attached by ayer's ligament through which the feeding vessels run primarily from the external carotid. A normal carotid body measures 3-5 mm in diameter. Afferent innervation appears to be provided through the glossopharyngeal nerve (the ninth cranial nerve). The glossopharyngeal nerve supplies motor fibers to the stylopharyngeus, parasympathetic secretomotor fibers to the parotid gland and sensory fibers to inter alia the tympanic cavity, interior surface of the soft palate and tonsils). Histologically, the carotid body includes Type I (chief) cells with copious cytoplasm and large round or oval nuclei. The cytoplasm contains dense core granules that apparently store and release catecholamines. The normal carotid body is responsible for detecting changes in the composition of arterial blood.

Carotid paragangliomas are rare tumors overall but are the most common form of head and neck paraganglioma. The treatment of choice for most carotid body paragangliomas is surgical excision. However, because of their location in close approximation to important vessels and nerves, there is a very real risk of morbidity (mainly cranial nerve X-XII deficits and vascular injuries) and mortality which is estimated as 3-9%. Tumor size is important because those greater than 5 cm in diameter have a markedly higher incidence of complications. Perioperative alpha and beta adrenergic blockers are given (if the carotid paraganglioma is secreting catecholamines) or less preferably angiographic embolization preoperatively. Radiotherapy, either alone or in conjunction with surgery, is a second consideration and an area of some controversy. Unfortunately, due to location and/or size, paragangliomas, including carotid paragangliomas can be inoperable.

2. Pheochromocytomas

Pheochromocytomas occur in the adrenal medulla and cause clinical symptoms related to excess catecholamine production, including sudden high blood pressure (hypertension), headache, tachycardia, excessive sweating while at rest, the development of symptoms after suddenly rising from a bent-over position, and anxiety attacks. Abdominal imaging and 24 hour urine collection for catecholamines are usually sufficient for diagnosis. Catecholamine blockade with phenoxybenzamine and metyrosine generally ameliorates symptoms and is necessary to prevent hypertensive crisis during surgery, the current therapy of choice. Standard treatment is laparoscopic adrenalectomy, although partial adrenalectomy is often used for familial forms of pheochromocytoma. Malignant (cancerous) pheochromocytomas are rare tumors.

Pheochromocytomas have been estimated to be present in approximately 0.3% of patients undergoing evaluation for secondary causes of hypertension. Pheochromocytomas can be fatal if not diagnosed or if managed inappropriately. Autopsy series suggest that many pheochromocytomas are not clinically suspected and that the undiagnosed tumor is clearly associated with morbid consequences.

The progression of changes in the adrenal medulla can be from normal adrenal medulla to adrenal medullary hyperplasia (a generalized increase in the number of cells and size of the adrenal medulla without the specific development of a tumor) to a tumor of the adrenal medulla (pheochromocytoma).

Treatment of a pheochromocytoma is surgical removal of one or both adrenal glands. Whether it is necessary to remove both adrenal glands will depend upon the extent of the disease. Patients who have had both adrenal glands removed must take daily cortisol and aldosterone replacement. Cortisol is replaced by either hydrocortisone, cortisone or prednisone and must be taken daily. Aldosterone is replaced by oral daily fludrocortisone (Florineftm). Increased amounts of replacement hydrocortisone or prednisone are required by such patients during periods of stress, including fever, cold, influenza, surgical procedure or anesthesia.

3. Glomus Tumors

Glomus tumors (a type of paraganglioma) are generally benign neoplasms, also arising from neuroectodermal tissues, found in various parts of the body. Glomus tumors are the most common benign tumors that arise within the temporal bone and fewer than five percent of them become malignant and metastasize. Glomus tumors arise from glomus bodies distributed along parasympathetic nerves in the skull base, thorax and neck. There are typically three glomus bodies in each ear. The glomus bodies are usually found accompanying Jacobsen's (CN IX) or Arnold's (CN X) nerve or in the adventitia of the jugular bulb. However, the physical location is usually the mucosa of the promontory (glomus tympanicums), or the jugular bulb (glomus jugulare).

The incidence of glomus jugulare tumors is about 1:1,300,000 population and the most striking bit of epidemiology is the predominant incidence in females with the female:male incidence ratio being at least 4:1. Catecholamine secreting (i.e. functional) tumors occur in about 1% to 3% of cases.

Glomus tumors have the potential to secrete catecholamines, similar to the adrenal medulla which also arises from neural crest tissue and can also secrete catecholamines. The neoplastic counterpart of a glomus tumor in the adrenal gland is the pheochromocytoma, and glomus tumors have been referred to as extra-adrenal pheochromocytoma. Catecholamine secreting glomus tumors can cause arrhythmia, excessive perspiration, headache, nausea and pallor.

Glomus tumors can arise in different regions of the skull base. When confined to the middle ear space, they are termed glomus tympanicum. When arising in the region of the jugular foramen, regardless of their extent, they are termed glomus jugulare. When they arise high in the neck, extending towards the jugular foramen, they are termed glomus vagale. When they arise in the area of the carotid bifurcation, they are called carotid body tumors. Other known sites of glomus tumors include the larynx, orbit, nose, and the aortic arch.

Glomus Jugulare tumors are the most common tumors of the middle ear. These tumors tend to be very vascular and are fed by branches of the external carotid artery. The symptoms of a glomus jugulare tumor include hearing loss with pulsatile ringing in the ear, dizziness, and sometimes ear pain. The patient can have a hearing loss due possibly to blockage of the middle ear, but also there can be a loss of hearing due to nerve injury from the tumor mass. Cranial nerve palsies of the nerves which control swallowing, gagging, shoulder shrugging and tongue movement can all be part of the presentation of glomus jugulare tumors. When the tympanic membrane is examined a red/blue pulsatile mass can often be seen. Symptoms are insidious in onset. Because of the location and the vascular nature of the tumors, a most common complaint is pulsatile tinnitus. It is believed that the tinnitus is secondary to mechanical impingement on the umbo is most cases. Other common symptoms are aural fullness, and (conductive) hearing loss.

Current therapy for a catecholamine secreting glomus tumor is irradiation and/or surgical ablation, preceded by administration of alpha and beta blockers. Treatment for glomus jugulare tumors includes administration of alpha and beta blockers. X-ray therapy can be used to improve symptoms even if the mass persists. It is also possible to embolize the tumor with materials which block its blood supply, however this procedure has associated problems with causing swelling of the tumor which can compress the brain stem and cerebellum as well as releasing the catecholamines from the cells which die when they lose their blood supply. Surgery can be carried out upon small tumors appropriately located. The complications of surgery for a glomus jugulare tumor are persistent leakage of cerebrospinal fluid from the ear and also palsy of one of the cranial nerves controlling face movement, sensation or hearing.

Even though the surgery may be successful glomus jugulare tumors are somewhat problematic because they have a high recurrence rate and may require multiple operations. Surgical ablation carries the risk of morbidity due mainly to iatrogenic cranial nerve deficits and CSF leaks. Lack of cranial nerve preservation is probably the most significant objection to surgical intervention because of the associated morbidity of lower cranial nerve deficits. Radiotherapy also has serious complications, including osteoradionecrosis of the temporal bone, brain necrosis, pituitary-hypothalamic insufficiency, and secondary malignancy. Other postoperative complications include CSF leaks, aspiration syndromes, meningitis, pneumonia and wound infections.

What is needed therefore is an effective, non-surgical ablation, non-radiotherapy therapeutic method for treating mammary gland neoplasms and precancerous hyperplastic mammary gland tissues.

SUMMARY

The present invention meets this need and provides an effective, non-surgical ablation, non-radiotherapy therapeutic method for treating various precancerous as well as cancerous mammary gland tissues. Thus, the present invention encompasses methods for treating atypical tissues, such as hyperplastic tissues, cysts and neoplasms (including tumors and cancers) and for preventing the development of, or for causing the regression or remission of, atypical tissues, cysts and neoplasms. In particular, the present invention encompasses methods for treating mammary gland disorders, such as mammary gland cysts and neoplasms, both benign and cancerous, as well as for treating hyperplastic and/or hypertonic mammary gland cells by local administration of a Clostridial toxin to or to the vicinity of the afflicted the mammary gland tissue.

An embodiment of the present invention is a method for treating a mammary gland disorder by local administration of between about $10^{-3}$ U/kg and about 2000 U/kg of a Clostridial neurotoxin to a mammary gland. The Clostridial neurotoxin can be a botulinum toxin. Preferably, the botulinum toxin is administered in an amount of between about $10^{-2}$ U/kg and about 200 U/kg. More preferably, the botulinum toxin is administered in an amount of between about $10^{-1}$ U/kg and about 35 U/kg. The botulinum toxin is selected from the group consisting of botulinum toxins types A, B, C, D, E, F and G and the preferred botulinum toxin is botulinum toxin type A.

The local administration of the botulinum toxin can be carried out by implantation of a botulinum toxin implant into or onto the mammary gland. The mammary gland disorder is selected from the group consisting of precancerous breast tissue and breast cancer. Thus, the mammary gland disorder can be cystic breast disease. The botulinum toxin can be locally administered by direct injection of the botulinum toxin into the mammary gland.

A more detailed embodiment of the present invention is a method for treating a mammary gland disorder by local administration of between about $10^{-3}$ U/kg and about 2000 U/kg of a botulinum toxin type A to a mammary gland of a human patient, thereby a mammary gland disorder.

Our invention also encompasses a method for treating a mammary gland disorder by local administration of a botulinum toxin to a mammary gland or to the vicinity of a precancerous breast tissue, thereby causing a reduction in the size and/or activity of a hyperplastic, hypertonic or neoplastic mammary gland tissue. This method can reduce the diameter of the hyperplastic, hypertonic or neoplastic mammary gland tissue by between about 20% and about 100%, subsequent to the local administration of the botulinum toxin.

Thus a method for treating a mammary gland disorder as disclosed herein can comprise the step of local administration of a therapeutic amount of a botulinum toxin to a hyperplastic, hypertonic or neoplastic mammary gland tissue, thereby causing a reduction in the diameter of the hyperplastic, hypertonic or neoplastic mammary gland tissue of between about 20% and about 100%.

Additionally, the present invention encompasses a method for preventing development of a mammary gland neoplasm, the method comprising the step of local administration of a botulinum toxin to a hyperplastic or hypertonic mammary gland tissue, thereby reducing a secretion from the hyperplastic or hypertonic mammary gland tissue and preventing the hyperplastic or hypertonic mammary gland tissue from developing into a neoplasm. In this method the botulinum toxin is administered in an amount of between about $10^{-3}$ U/kg and about 2,000 U/kg and the botulinum toxin is selected from the group consisting of botulinum toxin types A, B, C, D, E, F and G. The botulinum toxin can be locally administered by direct injection of the botulinum toxin into the hyperplastic or hypertonic mammary gland tissue.

To reiterate, a method for preventing development of a mammary gland neoplasm can comprise the step of local administration of a therapeutic amount of a botulinum toxin type A to the precancerous hyperplastic or hypertonic mammary gland tissue of a human patient, thereby preventing development of a mammary gland neoplasm.

Alternately, a method for preventing development of a neoplasm can comprise the step of local administration of between about $10^{-3}$ U/kg and about 2000 U/kg of a botulinum toxin to a hyperplastic tissue, wherein the botulinum toxin reduces a secretion from the hyperplastic tissue by inhibiting a vesicle mediated exocytosis from the precancerous hyperplastic tissue, thereby preventing development of the hyperplastic tissue into a neoplasm. The hyperplastic tissue can comprise a substrate for the botulinum toxin selected from the group of vesicle membrane docking proteins consisting of a 25 kiloDalton synaptosomal associated protein (SNAP-25), synaptobrevin and syntaxin. Furthermore, the botulinum toxin can be administered in an amount of between about 1 U and about 40,000 U, such as between about $10^{-3}$ U/kg and about 35 U/kg, between about $10^{-2}$ U/kg and about 25 U/kg, between about $10^{-2}$ U/kg and about 15 U/kg or between about 1 U/kg and about 10 U/kg. and the local administration of the botulinum toxin is carried out by implantation of a botulinum toxin implant into or onto the body of the breast tissue A detailed embodiment of the present invention is a method for preventing development of a mammary gland carcinoma (that is by preventing the development of a benign [though hyperplastic, metaplasic or atypical] precancerous breast tissue into a malignant neoplasm or carcinoma), the method comprising the step of local administration of between about $10^{-3}$ U/kg and about 2000 U/kg of a botulinum toxin type A to a hyperplastic, metaplasic or atypical breast tissue (such as an apocrine cell lined cyst) of a human patient, wherein the breast tissue comprises a substrate for the botulinum toxin selected from the group of vesicle membrane docking proteins consisting of a 25 kiloDalton synaptosomal associated protein (SNAP-25), synaptobrevin and syntaxin, and wherein the botulinum toxin acts upon the substrate to reduce a secretion from the afflicted breast tissue.

The present invention includes within its scope a method for treating a neoplasm by local administration of between about $10^{-3}$ U/kg and about 2000 U/kg of a botulinum toxin to the neoplasm, thereby treating the neoplasm by either reducing the size of the neoplasm and/or by reducing a secretion from the neoplasm.

A method according to the present invention can be carried out by direct injection of a botulinum toxin into the body of a neoplasm or by implantation of a botulinum toxin implant into or onto the body of the neoplasm. A method within the scope of the present invention can be practiced to locally administer between about $10^{-3}$ U/kg and about 2000 U/kg of a botulinum toxin to a neoplasm. U/kg means units of a botulinum toxin per kilogram of total patient weight. The botulinum toxin can be one of the botulinum toxin types A, B, $C_1$, D, E, F and G, and is preferably a botulinum toxin type A because of the known clinical efficacy of botulinum toxin type A for a number of indications and because of its ready availability.

Preferably, the botulinum toxin is administered in an amount of between about 1 U and about 40,000 U (total units, not per kg of patient weight). At the higher dose ranges the amount of botulinum toxin administered (i.e. 40,000 units) can be administered in the form of a controlled release delivery system (i.e. an implant), whereby fractional amounts of the botulinum toxin depot (i.e. about 10 units of a botulinum toxin type A or about 500 units of a botulinum toxin type B) are released from the controlled release delivery system over a three to four month period (continuous release delivery system) or is released from the controlled release delivery system in a multiphasic manner in approximate three to four month repeating cycles (pulsatile release delivery system). Suitable controlled release delivery systems to use in the present invention for either the continuous or pulsatile intra or peri-neoplasm release of therapeutic amounts of a botulinum toxin are disclosed in co-pending application Ser. No. 09/587, 250 entitled "Neurotoxin Implant" and Ser. No. 09/624,003 entitled "Botulinum Toxin Implant".

In a more preferred embodiment of the present invention, the amount of a botulinum toxin type A locally administered to the body of or to a site within the body of the neoplasm according to the present invention can be an amount between about $10^{-3}$ U/kg and about 40 U/kg. Less than about $10^{-3}$ U/kg of a botulinum toxin type A is not expected to result in a significant therapeutic efficacy, while more than about 40 U/kg of a botulinum toxin type A can be expected to result in a toxic or near toxic dose of the toxin. With regard to a botulinum toxin type B, the amount of a botulinum toxin type B locally administered to the neoplasm according to the present invention can be an amount between about $10^{-3}$ U/kg and about 2000 U/kg. Less than about $10^{-3}$ U/kg of a botulinum toxin type B is not expected to result in a significant therapeutic efficacy, while more than about 2000 U/kg of a botulinum toxin type B can be expected to result in a toxic or near toxic dose of the type B toxin. It has been reported that about 2000 units/kg, intramuscular, of a commercially available botulinum toxin type B preparation approaches a primate lethal dose of type B botulinum toxin. Meyer K. E. et al, *A Comparative Systemic toxicity Study of Neurobloc in Adult and Juvenile Cynomolgus Monkeys*, Mov. Disord 15(Suppl 2); 54; 2000. With regard to the botulinum toxins types C, D, E, F and G, amounts for injection into a neoplasm can be determined on a patient by patient basis and are not expected to exceed the type B toxin dose range.

In a more preferred embodiment of the present invention, the amount of a type A botulinum toxin administered according to the disclosed methods is between about $10^{-2}$ U/kg and about 25 U/kg. Preferably, the amount of a type B botulinum toxin administered by a continuous release system during a given period is between about $10^{-2}$ U/kg and about 1000 U/kg, since it has been reported that less than about 1000 U/kg of type B botulinum toxin can be intramuscularly administered to a primate without systemic effect. Ibid. More preferably, the type A botulinum toxin is administered in an amount of between about $10^{-1}$ U/kg and about 15 U/kg. Most preferably, the type A botulinum toxin is administered in an amount of between about 1 U/kg and about 10 U/kg. In many instances, an intra-neoplastic administration of from about 1 units to less than about 100 units of a botulinum toxin type A, can provide effective and long lasting therapeutic relief, as set forth herein. More preferably, from about 5 units to about 75 units of a botulinum toxin, such as a botulinum toxin type A, can be used and most preferably, from about 5 units to about 50 units of a botulinum toxin type A, can be locally administered into a target neoplasm tissue with efficacious results. In a particularly preferred embodiment of the present invention from about 1 units to about 50 units of a botulinum toxin, such as botulinum toxin type A, can be locally administered to a neoplasm target tissue with therapeutically effective results, as described herein.

A detailed method within the scope of the present invention can be carried out by local administration of between about $10^{-3}$ U/kg and about 2000 U/kg of a botulinum toxin type A to a neoplasm of a human patient, thereby reducing a secretion from the neoplasm.

"Local administration" means direct injection of the neurotoxin into or to the local area of the target tissue. Systemic routes of administration, such as oral and intravenous routes of administration, are excluded from the scope of the present invention.

The botulinum toxin can be a modified botulinum toxin, that is the botulinum toxin can have at least one of its amino acids deleted, modified or replaced, as compared to a native botulinum toxin. Thus, the botulinum toxin can be a recombinant produced botulinum toxin or a derivative or fragment thereof.

DESCRIPTION

The present invention is based upon the discovery that hyperplastic, hypertonic, cystic and/or neoplastic tissues can be treated with a Clostridial toxin to thereby reduce or eliminate the hyperplasia, hypertonia, cystic and/or neoplastic condition. The tissue treated can be benign or malignant and hyperplasia includes a hypertonic condition. The present invention is therefore applicable to the treatment of conditions which include breast cancer, cystic breast disease, lung cancer, adenocarcinomas, ovarian cancer, oral and oropharyngeal cancers, pancreatic cysts and pancreatic cancer, prostate cancer, kidney cancer, GI tract cancer, testicular cancer and cysts, lymph node cancer, endometrial cancers, as well as to hyperplastic, metaplasic, atypia and dysplasic precancerous tissues of such organs and glands.

Additionally, excessively secreting cells (hyperplastic or hypertonic) wherein the secretory activity is controlled or influenced by one or more of the botulinum toxin substrates can be treated by a method within the scope of the present invention so as to prevent the development of the hyperplastic or hypertonic secretory tissue into a neoplasm. In the target tissue the proteolytic light chain of the botulinum toxin is internalized.

In a preferred embodiment the present invention is a method for treat breast disease, such as precancerous breast tissues. Although the present invention is not limited to any particular mechanism, it can be hypothesized that local administration of a Clostridial toxin (such as a botulinum toxin) to an afflicted tissue, such as a breast cyst, results in treatment of the i.e. cyst (i.e. reduction of [or total elimination of] size the cyst, and/or of the apocrine cell hyperplasia) due to either an inhibitory effect of the toxin upon stimulatory cholinergic fibers which innervate the apocrine cells or a direct effect of the toxin upon the cyst upon internalization of the toxin (or at least of the toxin light chain) by cyst cells.

Thus a preferred embodiment of the present invention is a method for treating a precancerous mammary gland disorder, such as breast cysts, sclerosing adenosis, papillomas, fibroadenomas (hyperplasia lobules) and blunt duct adenosis. By precancerous it is meant that the afflicted breast tissue is not-malignant (i.e. is not cancerous), although it can be hyperplastic, hypertrophic or metaplasic, and that the presence of the precancerous tissue increases the risk to the patient of development of a breast cancer.

Thus, cholinergically innervated target tissues can be treated by local administration of a Clostridial toxin, such as a botulinum toxin. By local administration it is meant that the neurotoxin is administered directly into, or to the vicinity of the target tissue (i.e. a precancerous breast tissue) or local tissue area to be treated. Local administration includes injection of the neurotoxin directly into the afflicted tissue. Noncancerous (benign), precancerous, cancerous (malignant) hyperplastic and/or hypertonic secretory tissues can be treated by a method within the scope of the present invention. Nodular or diffuse hyperplasia which precedes tumor development can be treated by the present method.

It has been discovered that a particular neurotoxin, botulinum toxin, can be used with dramatic ameliorative effect to treat a variety of precancerous breast tissues, thereby significantly superseding current surgical, chemotherapy and radiotherapy therapeutic methods. Significantly, a single local administration of the botulinum toxin can be used to successfully treat a breast disease.

The route of administration and amount of botulinum toxin administered can vary widely according to the particular mammary gland disorder being treated and various patient variables including size, weight, age, disease severity and responsiveness to therapy. Method for determining the appropriate route of administration and dosage are generally determined on a case by case basis by the attending physician. Such determinations are routine to one of ordinary skill in the art (see for example, *Harrison's Principles of Internal Medicine* (1997), edited by Anthony Fauci et al., 14$^{th}$ edition, published by McGraw Hill). Treatment is carried out so as to substantially avoiding entry of the toxin into the systemic circulation (i.e. by use of subcutaneous or intramuscular injection as opposed to intravenous administration).

The specific dosage appropriate for administration is readily determined by one of ordinary skill in the art according to the factors discussed above. The dosage can also depend upon the size of the tumor to be treated or denervated, and the commercial preparation of the toxin. Additionally, the estimates for appropriate dosages in humans can be extrapolated from determinations of the amounts of botulinum required for effective denervation of other non-neoplastic tissues. Thus, the amount of botulinum A to be injected is proportional to the mass and level of activity of the breast tissue to be treated. Generally, between about 0.01 and 2000 units per kg of patient weight of a botulinum toxin, such as botulinum toxin type A, can be administered to effectively accomplish a toxin induced target tissue atrophy upon administration of the neurotoxin at or to the vicinity of the breast target tissue. Less than about 0.01 U/kg of a botulinum toxin does not have a significant therapeutic effect while more than about 2000 U/kg or 35 U/kg of a botulinum toxin B or A, respectively, approaches a toxic dose of the specified botulinum toxin. Careful placement of the injection needle and a low volume of neurotoxin used prevents significant amounts of botulinum toxin from appearing systemically. A more preferred dose range is from about 0.01 U/kg to about 25 U/kg of a botulinum toxin, such as that formulated as BOTOX®. The actual amount of U/kg of a botulinum toxin to be administered depends upon factors such as the extent (mass) and level of activity of the i.e. hyperplastic breast tissue to be treated and the administration route chosen. Botulinum toxin type A is a preferred botulinum toxin serotype for use in the methods of the present invention.

The main site of action of botulinum toxin is the neuromuscular junction where the toxin binds rapidly and prevents the release of acetylcholine. Thus, while it is known that the botulinum toxins have a known binding affinity for cholinergic, pre-synaptic, peripheral motor neurons, we have discovered that the botulinum toxins can also bind to and translocate into a variety of precancerous breast tissues, where the toxin then acts, in the known manner, as an endoprotease upon its respective secretory vessel-membrane docking protein. Because of the lower affinity of the botulinum toxins for certain breast tissues, the toxin can preferably injected into secretory or glandular tissues to provide a high local concentration of the toxin. Thus, the present invention is applicable to the treatment of precancerous breast tissues which may have with little or no cholinergic innervation.

Preferably, a neurotoxin used to practice a method within the scope of the present invention is a botulinum toxin, such as one of the serotype A, B, C, D, E, F or G botulinum toxins. Preferably, the botulinum toxin used is botulinum toxin type A, because of its high potency in humans, ready availability, and known use for the treatment of skeletal and smooth muscle disorders when locally administered by intramuscular injection.

A route for administration of a neurotoxin according to the present disclosed invention for treating a precancerous breast tissue can be selected based upon criteria such as the solubility characteristics of the neurotoxin toxin chosen as well as the amount of the neurotoxin to be administered. The amount of the neurotoxin administered can vary widely according to the particular disorder being treated, its severity and other various patient variables including size, weight, age, and responsiveness to therapy. For example, the extent of the precancerous breast tissue influenced is believed to be proportional to the volume of neurotoxin injected, while the quantity of the denervation is, for most dose ranges, believed to be proportional to the concentration of neurotoxin injected. Methods for determining the appropriate route of administration and dosage are generally determined on a case by case basis by the attending physician. Such determinations are routine to one of ordinary skill in the art (see for example, Harrison's Principles of Internal Medicine (1997), edited by Anthony Fauci et al., 14th edition, published by McGraw Hill).

The present invention includes within its scope the use of any neurotoxin which has a long duration therapeutic effect when locally applied to a precancerous breast tissue of a patient. For example, neurotoxins made by any of the species of the toxin producing *Clostridium* bacteria, such as *Clostridium botulinum*, *Clostridium butyricum*, and *Clostridium beratti* can be used or adapted for use in the methods of the present invention. Additionally, all of the botulinum serotypes A, B, C, D, E, F and G can be advantageously used in the practice of the present invention, although type A is the most preferred serotype, as explained above. Practice of the present invention can provide target tissue atrophy and remission for 27 months or longer in humans.

It is known that catecholamine release from permeabilized adrenal medulla cells can be inhibited by a botulinum toxin. Additionally, it is known that release of insulin from permeabilized (as by electroporation) insulin secreting cells can be inhibited by a botulinum toxin. When in vitro, the cell membranes of these non-nerve cells can be permeabilized to assist introduction of a botulinum toxin into the cell's cytosol due to the lack of cell surface receptors for a botulinum toxin. Thus, botulinum toxin type B apparently inhibits insulin secretion by cleaving synaptobrevin present in the insulin secreting cell line HIT-15. Boyd R. S., et al *The Effect of Botulinum Neurotoxin-B On Insulin Release From a Beta Cell*, Mov Disord 10(3):376 (1995). It is the inventor's contention that a botulinum toxin can block the release of any vesicle mediated exocytosis from any secretory (i.e. neuronal, glandular, secretory, chromaffin) cell type, as long as the light chain of the botulinum toxin is translocated into the intracellular medium. For example, the intracellular protein SNAP-25 is widely distributed in both neuronal and non-neuronal secretory cells and botulinum toxin type A is an endopeptidase for which the specific substrate is SNAP-25. Thus, while cholinergic neurons have a high affinity acceptor for the botulinum and tetanus toxins (and are therefore more sensitive than other neurons and other cells to the inhibition of vesicle mediated exocytosis of secretory compounds), as the toxin concentration is raised, non-cholinergic sympathetic neurons, chromaffin cells and other cell types can take up a botulinum toxin and show reduced exocytosis.

Hence, by practice of the present disclosed invention, non-cholinergic nerve fibers as well as non or poorly innervated secretory neoplasms can be treated by use of an appropriately higher concentration of a botulinum toxin to bring about therapeutic atrophy of secretory neoplasms (i.e. treatment of functional (catecholamine secreting) paragangliomas) and hyperplastic chromaffin cells.

In the normal adrenal medulla, the catecholamine secretion rate is controlled by the activity of the nerves stimulating the chromaffin cells. Contrary to the general belief that the pheochromocytomas are not innervated and that the release of catecholamines from such tumors is not under nervous control, there is evidence for cholinergic innervation of such tumors. For example, electron microscopy has demonstrated a nerve with small synaptic vesicles in contact with cells containing catecholamine vesicles. Additionally, the sudden secretion of catecholamines from a pheochromocytomas into the circulation precipitated by an emotional upset, hypotension or hyperventilation points to a nervous system influence on the secretion. Furthermore, the tilting a patient with a pheochromocytoma from a horizontal to an upright position has been shown to cause an exaggerated increase in urinary norepinephrine not seen in subjects with such a tumor and this may effect result from (a) a mechanical effect (i.e. compression of the catecholamine rich tumor) (b) reflex activation of the sympathetic system in which adrenergic system increased amounts of catecholamines may have accumulated in the nerve endings of a patient with a pheochromocytoma and/or (b) activation of existing pheochromocytoma innervation.

Furthermore, a method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone. Improved patient function is synonymous with an improved quality of life (QOL). QOL can be assesses using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality, and general health perceptions. Scores obtained can be compared to published values available for various general and patient populations.

As set forth above, we have discovered that a surprisingly effective and long lasting therapeutic effect can be achieved by local administration of a neurotoxin to a precancerous breast tissue of a human patient. In its most preferred embodiment, the present invention is practiced by direct injection into the target tissue or to the local area of the target tissue of botulinum toxin type A. It has been reported that at the neuroglandular junction, the chemical denervation effect of a botulinum toxin, such as botulinum toxin type A, has a considerably longer duration of action, i.e. 27 months vs. 3 months.

The present invention does include within its scope: (a) neurotoxin complex as well as pure neurotoxin obtained or processed by bacterial culturing, toxin extraction, concentration, preservation, freeze drying and/or reconstitution and; (b) modified or recombinant neurotoxin, that is neurotoxin that has had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made, and includes neurotoxins with one or more attached targeting moieties for chromaffin and neoplasm cells types.

Botulinum toxins for use according to the present invention can be stored in lyophilized or vacuum dried form in containers under vacuum pressure. Prior to lyophilization the botulinum toxin can be combined with pharmaceutically acceptable excipients, stabilizers and/or carriers, such as albumin. The lyophilized or vacuum dried material can be reconstituted with saline or water.

In each of the following examples, the specific amount of a botulinum toxin administered depends upon a variety of factors to be weighed and considered within the discretion of the attending physician and in each of the examples insignificant amounts of botulinum toxin enter appear systemically with no significant side effects. Units of botulinum toxin injected per kilogram (U/kg) below are per kg of total patient weight. For example, 3 U/kg for a 70 kg patient calls for an injection of 210 units of the botulinum toxin.

EXAMPLES

The following examples provide those of ordinary skill in the art with specific preferred methods within the scope of the present invention for carrying out the present invention and are not intended to limit the scope of what the inventors regards as their invention.

In each of the following examples, the specific amount of a botulinum toxin (such as BOTOX®) administered depends upon a variety of factors to be weighed and considered within the discretion of the attending physician and in each of the examples insignificant amounts of botulinum toxin appear systemically with no significant Example One Use of a Botulinum Toxin to Treat Precancerous Mammary Gland Disorders 1. Treatment of Cysts A 46 year old female presents with chronic cystic disease in otherwise normal breasts. A fibrocystic change appears as a mixture of a number of benign entities with a total mass 1.2 cm in diameter and containing areas of firm fibro-fatty tissue and multiple cysts of varying size. Ultrasound and imaging investigation reveals cyst formation and microcalcification. Histological examination reveals the present of apocrine atypia (both hyperplasia and metaplasia) and the patient is therefore determined to be at risk for development of apocrine carcinoma or medullary carcinoma.

Fine needle aspiration (FNA) of palpable breast has been used since 1930 to examine the cytopathology of breast cells in the diagnosis of cancer. Stereotactic fine needle aspiration as well as ultrasound and mammographic guided fine needle aspiration has also been used for nonpalpable lesions. Stereoradiography can be done using standard mammography equipment and compression plates to allow precise positioning of the fine needle along the x and y coordinates to within 1 mm of the lesion. Ultrasound guidance is very useful in determining if the lesion is purely cystic, mixed or solid. Typically a 22 gauge needle is used. The same methodology used for FNA is used to inject a botulinum toxin into a target tissue. Thus, for injection the needle can be attached to a syringe with or without a special handle that permits a single-handed grip. The skin is wiped with an antiseptic. The breast mass is grasped and the overlying skin pulled taut into a position favorable for the operator to insert the needle with his or her other hand. The needle is inserted into the mass and the plunger of the syringe containing a solution of a botulinum toxin is pushed forward while the needle proceeds in a straight line through the lesion. Alternately, for extended therapeutic effect, a controlled release implant can be inserted subcutaneously and/or a suspension of botulinum containing microspheres can be injected, as set forth in U.S. Pat. Nos. 6,306,423 and 6,312,708.

Local administration (injection) of from 10 unit to 100 units of a botulinum toxin type A, such as BOTOX®, into the cyst mass is carried out. Within 28 days thereafter the cyst has substantially regressed (cyst diameter reduced by at least 80%) and remains so for the ensuing 2 to 24 months. Alternately, a botulinum toxin type B, C, D, E, F or G can be administered, with the dosing amount adjusted to reflect the differing potency as compared to the type A toxin. Thus, for example, since botulinum toxin type B is known to be about 50 times less potent that botulinum toxin type A, from 500 to 5000 unit of type B toxin is local administered.

2. Treatment of Sclerosing Adenosis

A 59 year old post-menopausal female with a breast pain complaint is examined. Mammography reveals a proliferative lesion arising from the terminal duct lobular unit and comprising a clinically palpable mass 1.3 cm in diameter with no specific coloration. The mass is ill defined and there is some pain and tenderness. Histologically, normal configuration of a group of lobules is distorted by a disorderly proliferation of acini and intralobular stromal cells. Local administration (injection) of from 10 unit to 100 units of a botulinum toxin type A, such as BOTOX®, into the mass is carried out. Within 28 days thereafter the mass has substantially regressed (diameter reduced by at least 80%) and remains so for the ensuing 2 to 24 months. Alternately, a botulinum toxin type B, C, D, E, F or G can be administered, with the dosing amount adjusted to reflect the differing potency as compared to the type A toxin. Thus, for example, since botulinum toxin type B is known to be about 50 times less potent that botulinum toxin type A, from 500 to 5000 unit of type B toxin can be locally administered.

3. Treatment of Duct Papillomas

A 50 year old female with a history of bloodstained discharge from one nipple is examined. Although there is no palpable mass, a benign neoplasm of the ductal epithelium of the breast is revealed. Local administration of from 10 unit to 100 units of a botulinum toxin type A, such as BOTOX®, is carried out. Within 28 days thereafter the discharge has resolved and the patient remains symptom free remains so for the ensuing 2 to 24 months. Alternately, a botulinum toxin type B, C, D, E, F or G can be administered, with the dosing amount adjusted to reflect the differing potency as compared to the type A toxin. Thus, for example, since botulinum toxin type B is known to be about 50 times less potent that botulinum toxin type A, from 500 to 5000 unit of type B toxin can be locally administered.

4. Treatment of Fibroadenomas

A 36 year old female presents with a lump in the breast. Clinical examination, imaging (mammography) and fine needle aspiration cytology reveals a firm, mobile, well-defined, painless, rubbery mass, 1.5 cm in diameter. Since the legion is benign, the patent is offered local injection botulinum toxin as an alternative to excision and informed consent is obtained thereto. Local administration into the lump of from 10 unit to 100 units of a botulinum toxin type A, such as BOTOX®, is carried out. Within 28 days thereafter the mass has substantially regressed (diameter reduced by at least 80%) and so remains for the ensuing 2 to 24 months. Alternately, a botulinum toxin type B, C, D, E, F or G can be administered, with the dosing amount adjusted to reflect the differing potency as compared to the type A toxin. Thus, for example, since botulinum toxin type B is known to be about 50 times less potent that botulinum toxin type A, from 500 to 5000 unit of type B toxin can be locally administered.

5. Treatment of Blunt Duct Adenosis

At 54 year old female with a history of caffeine ingestion (4-6 cups of coffee a day for about the last 10 years) has columnar alteration of lobules determined as ill defined areas of microcyst formation with individual terminal duct lobular units showing alteration or replacement of the normal luminal epithelial layer by a single layer of taller columnar epithelial cells with basally placed nuclei and cytoplasmic apical snouts. Local administration into the lump of from 10 unit to 100 units of a botulinum toxin type A, such as BOTOX®, is carried out. Within 28 days thereafter the adenosis has resolved and remains so for the ensuing 2 to 24 months. Alternately, a botulinum toxin type B, C, D, E, F or G can be administered, with the dosing amount adjusted to reflect the differing potency as compared to the type A toxin. Thus, for example, since botulinum toxin type B is known to be about 50 times less potent that botulinum toxin type A, from 500 to 5000 unit of type B toxin can be locally administered 6. Treatment of Proliferative Breast Disease Histology upon a biopsy specimen from A 64 year old female reveals epithelial hyperplasia (proliferative with atypia) as shown by an increase in cell number above the normal bilayer of normal luminal epithelial cell and myoepithelail cell. Local administration into the lump of from 10 unit to 100 units of a botulinum toxin type A, such as BOTOX®, is carried out. Within 28 days thereafter biopsy followed by histological examination determines the patient to be free of atypia and she remains do for at least the ensuing 2 to 24 months. Alternately, a botulinum toxin type B, C, D, E, F or G can be administered, with the dosing amount adjusted to reflect the differing potency as compared to the type A toxin. Thus, for example, since botulinum toxin type B is known to be about 50 times less potent that botulinum toxin type A, from 500 to 5000 unit of type B toxin can be locally administered Example 2

Treatment of Hypertonic or Hyperplastic Tissues with a Botulinum Toxin

Local administration of a botulinum toxin directly to or to the vicinity of a hypertonic or hyperplastic target tissue can be accomplished by several methods. As set forth above a dermal or subdermal target tissue, such as breast tissue, can be treated by direct injection or by placement of a toxin implant. Visceral sites, such as a visceral neuroblastoma, can also be easily accessed. For example, endoscopy for diagnostic and therapeutic purposes is well known.

(1) Therapeutic pancreatic endoscopic techniques include pancreatic sphincterotomy, stricture dilation, stenting, pseudocyst drainage and endoscopic retrograde cholangio-pancreatography (ERCP) which permits visualization of and treatment of the pancreatic-biliary ductal system. An endoscope used for pancreatic therapy can be modified to permit its use for direct injection of a neurotoxin, such as a botulinum toxin directly into pancreatic tissue. See for example U.S. Pat. No. 5,674,205. For the purposes of the present invention, the endoscope is moved from the oropharynx through the stomach, duodenum, and finally into the pancreatic duct, duct decompression having been carried out previously (for example by dilation or stenting), if required, to permit lodgment of the endoscope in the duct. Once so located, a hollow needle tip can be extended from the endoscope into pancreatic tissue and through which needle the neurotoxin can be injected into the pancreatic tissue.

If the pancreatic duct is not accessible or does not decompress, a percutaneous needle, imaging guided (i.e. by ultrasound or computed tomography) can also be used for transabdominal injection of a neurotoxin directly into pancreatic tissue. Thus, percutaneous needle aspiration for pancreatic biopsy is a known technique and aspiration can be reversed to accomplish the desired toxin injection. Thus, an insulinoma or hypertonic or hyperplastic pancreatic tissue can be treated by local administration of from 1 500 units of a botulinum toxin to the pancreatic target tissue. Neoplastic or hyperplastic lung, intestinal and ovarian target tissue can likewise be treated, (2) Pituitary Stereotactic procedures can be used for precise intracranial administration of neurotoxin in aqueous form or as an implant to treat a hyperplasic or hypothalamus or pituitary target tissue. A cranial neuroblastoma is also treated in this manner. Thus, intracranial administration of a botulinum toxin can be carried out as follows.

A preliminary MRI scan of the patient can be carried out to obtain the length of the anterior commissure-posterior commissure line and its orientation to external bony landmarks. The base of the frame can then be aligned to the plane of the anterior commissure-posterior commissure line. CT guidance is used and can be supplemented with ventriculography. The posterior commissure can be visualized on 2-mm CT slices and used as a reference point.

Physiological corroboration of target tissue localization can be by use of high and low frequency stimulation through a electrode accompanying or incorporated into the long needle syringe used. A thermistor electrode 1.6 mm in diameter with a 2 mm exposed tip can be used (Radionics, Burlington, Mass.). With electrode high frequency stimulation (75 Hz) paraesthetic responses can be elicited in the forearm and hand at 0.5-1.0 V using a Radionics lesion generator (Radionics Radiofrequency Lesion Generator Model RFG3AV). At low frequency (5 Hz) activation or disruption of tremor in the affected limb occurred at 2-3 V. With the methods of the present invention, the electrode is not used to create a lesion. Following confirmation of target tissue localization, a neurotoxin can be injected, thereby causing a reversible, chemical hypothalamectomy. A typical injection is the desired number of units (i.e. about 0.1 to about 5 units of a botulinum toxin type A complex in about 0.01 ml to about 0.1 ml of water or saline. A low injection volume can be used to minimize toxin diffusion away from target. Typically, the hypothalamic releasing factor or pituitary hormone release inhibition effect can be expected to wear off within about 2-4 months. Thus, an alternate neurotoxin format, neurotoxin incorporated within a polymeric implant, can be used to provide controlled, continuous release of a therapeutic amount of the toxin at the desired location over a prolonged period (i.e. from about 1 year to about 6 years), thereby obviating the need for repeated toxin injections.

Several methods can be used for stereotactically guided injection of a neurotoxin to various intracranial targets, such as the arcuate nucleus (AN) for treatment of acromegaly. Thus a stereotactic magnetic resonance (MRI) method relying on three-dimensional (3D) T1-weighted images for surgical planning and multiplanar T2-weighted images for direct visualization of the AN, coupled with electrophysiological recording and injection guidance for AN injection can be used. See e.g. Bejjani, B. P., et al., *Bilateral Subthalamic Stimulation for Parkinson's Disease by Using Three-Dimensional Stereotactic Magnetic Resonance Imaging and Electrophysiological Guidance*, J Neurosurg 92(4); 615-25:2000. The coordinates of the center of the AN can be determined with reference to the patient's anterior commissure-posterior commissure line and a brain atlas.

Electrophysiological monitoring through several parallel tracks can be performed simultaneously to define the functional target accurately. The central track, which is directed at the predetermined target by using MRI imaging, can be selected for neurotoxin injection. No surgical complications are expected.

Computer-aided atlas-based functional neurosurgery methodology can be used to accurately and precisely inject the desired neurotoxin or implant a neurotoxin controlled release implant. Such methodologies permit three-dimensional display and real-time manipulation of hypothalamic structures. Neurosurgical planning with mutually preregistered multiple brain atlases in all three orthogonal orientations is therefore possible and permits increased accuracy of target definition for neurotoxin injection or implantation, reduced time of the surgical procedure by decreasing the number of tracts, and facilitates planning of more sophisticated trajectories. See e.g. Nowinski W. L. et al., *Computer-Aided Stereotactic Functional Neurosurgery Enhanced by the Use of the Multiple Brain Atlas Database*, IEEE Trans Med Imaging 19(1), 62-69:2000. Thus, an pituitary tumor or hypertonic or hyperplastic pituitary tissue can be treated by local administration of from 1 to 500 units of a botulinum toxin to the pituitary target tissue.

Methods according to the invention disclosed herein has many advantages, including the following:

(1) the invention renders unnecessary surgery for effective treatment of diverse breast disease, including hyperplastic, hypertonic and metaplasic breast tissues.

(2) systemic drug effects can be avoided by direct local application of a neurotoxin according to the present invention (3) the ameliorative effects of the present invention can persists for two years or longer from a single local administration of a neurotoxin as set forth herein.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes local otic administration methods wherein two or more neurotoxins, such as two or more botulinum toxins, are administered concurrently or consecutively. For example, botulinum toxin type A can be administered until a loss of clinical response or neutralizing antibodies develop, followed by administration of botulinum toxin type E. Alternately, a combination of any two or more of the botulinum serotypes A-G can be locally administered to control the onset and duration of the desired therapeutic result. Furthermore, non-neurotoxin compounds can be administered prior to, concurrently with or subsequent to administration of the neurotoxin to proved adjunct effect such as enhanced or a more rapid onset of denervation before the neurotoxin, such as a botulinum toxin, begins to exert its therapeutic effect.

Our invention also includes within its scope the use of a neurotoxin, such as a botulinum toxin, in the preparation of a medicament for the treatment of a precancerous breast tissue by local administration of the neurotoxin.

Accordingly, the spirit and scope of the following claims should not be limited to the descriptions of the preferred embodiments set forth above.

What is claimed is:

1. A method for treating a breast for the following disorders: chronic cystic disease, sclerosing adenosis, duct papillomas, fibroadenoma, blunt duct adenosis and epithelial hyperplasia, the method comprising the step of local administration of a botulinum toxin type A to a hyperplastic tissue of said breast, wherein the botulinum toxin reduces a secretion from the hyperplastic tissue by inhibiting a vesicle mediated exocytosis from the hyperplastic tissue, thereby treating the chronic cystic disease, sclerosing adenosis, duct papillomas, fibroadenoma, blunt duct adenosis and epithelial hyperplasia.

2. The method of claim 1 wherein the hyperplastic tissue comprises a substrate for the botulinum toxin selected from the group of vesicle membrane docking proteins consisting of a 25 kiloDalton synaptosomal associated protein (SNAP-25), synaptobrevin and syntaxin.

3. The method of claim 2, wherein the botulinum toxin is administered in an amount of between about 1 U and about 40,000 U.

4. The method of claim 2, wherein the botulinum toxin is administered in an amount of between about 10-3 U/kg and about 35 U/kg.

5. The method of claim 2, wherein the botulinum toxin is administered in an amount of between about 10-2 U/kg and about 25 U/kg.

6. The method of claim 2, wherein the botulinum toxin is administered in an amount of between about 10-2 U/kg and about 15 U/kg.

7. The method of claim 2, wherein the botulinum toxin is administered in an amount of between about 1 U/kg and about 10 U/kg.

8. The method of claim 2, wherein local administration of the botulinum toxin is carried out by implantation of a botulinum toxin implant.

9. The method of claim 2, wherein the botulinum toxin is locally administered by direct injection of the botulinum toxin.

* * * * *

UNITED STATES PATENT AND TRADEMARK OFFICE
CERTIFICATE OF CORRECTION

| | |
|---|---|
| PATENT NO. | : 7,846,456 B2 |
| APPLICATION NO. | : 11/192777 |
| DATED | : December 7, 2010 |
| INVENTOR(S) | : Mitchell F. Brin |

It is certified that error appears in the above-identified patent and that said Letters Patent is hereby corrected as shown below:

On Title page, in field (56), under "OTHER PUBLICATIONS", in column 2, line 9, delete "stategies" and insert -- strategies --, therefor.

Title page 2, under "OTHER PUBLICATIONS", in column 1, line 4, delete "portio nof th emammary" and insert -- portion of the mammary --, therefor.

Title page 2, under "OTHER PUBLICATIONS", in column 1, line 14, delete "Insulni" and insert -- Insulin --, therefor.

Title page 2, under "OTHER PUBLICATIONS", in column 1, line 52, before "A.R.," delete "Neuroblastoma".

Title page 2, under "OTHER PUBLICATIONS", in column 1, line 63, delete "Toxin,and" and insert -- Toxin and --, therefor.

Title page 2, under "OTHER PUBLICATIONS", in column 2, line 62, delete "Syunaptobrevin," and insert -- Synaptobrevin, --, therefor.

In column 1, line 45, delete "Spyridis" and insert -- Sivridis --, therefor.

In column 1, line 51, after "136-65" insert -- . --.

In column 1, line 56, delete "tubuol-alveolar" and insert -- tubular-alveolar --, therefor.

In column 2, line 13, delete "woman" and insert -- women --, therefor.

In column 2, line 25, delete "fibroademoma" and insert -- fibroadenoma --, therefor.

In column 4, line 15, delete "fibroademoma," and insert -- fibroadenoma, --, therefor.

Signed and Sealed this
Tenth Day of May, 2011

David J. Kappos
*Director of the United States Patent and Trademark Office*

CERTIFICATE OF CORRECTION (continued)
U.S. Pat. No. 7,846,456 B2

In column 12, line 54, delete "mammososmatotroph" and insert -- mammosomatotroph --, therefor.

In column 13, line 14, after "cells"" insert -- . --.

In column 14, line 23, delete "splancnic" and insert -- splanchnic --, therefor.

In column 18, line 57, after "tissue" insert -- . --.

In column 25, line 2, after "significant" insert -- . --.

In column 26, line 59, after "administered" insert -- . --.

In column 26, line 64, delete "myoepithelail" and insert -- myoepithelial --, therefor.

In column 27, line 8-9, after "administered" insert -- . --.

In column 27, line 52, delete "treated," and insert -- treated. --.

In column 28, line 15, delete "hypothalamectomy." and insert -- hypothalamotomy. --, therefor.

In column 28, line 64, delete "19(1)," and insert -- 19(1); --, therefor.

In column 30, line 21, in claim 4, delete "10-3" and insert -- $10^{-3}$ --, therefor.

In column 30, line 24, in claim 5, delete "10-2" and insert -- $10^{-2}$ --, therefor.

In column 30, line 27, in claim 6, delete "10-2" and insert -- $10^{-2}$ --, therefor.